US008916141B2

United States Patent
Sung et al.

(10) Patent No.: US 8,916,141 B2
(45) Date of Patent: Dec. 23, 2014

(54) HYALURONIDASE INHIBITOR CONTAINING POLY-GAMMA-GLUTAMIC ACID AS AN EFFECTIVE COMPONENT

(75) Inventors: Moon Hee Sung, Daejeon (KR); Chung Park, Daejeon (KR); Jae Chul Choi, Daejeon (KR); Hiroshi Uyama, Shiga (JP); So Lim Park, Busan (KR)

(73) Assignee: Bioleaders Corporation, Yongsan-Dong, Yuseong-Gu (KR)

( * ) Notice: Subject to any disclaimer, the term of this patent is extended or adjusted under 35 U.S.C. 154(b) by 1012 days.

(21) Appl. No.: 12/090,678

(22) PCT Filed: Oct. 31, 2005

(86) PCT No.: PCT/KR2005/003632
§ 371 (c)(1),
(2), (4) Date: Jun. 21, 2008

(87) PCT Pub. No.: WO2007/046569
PCT Pub. Date: Apr. 26, 2007

(65) Prior Publication Data
US 2008/0247986 A1    Oct. 9, 2008

(30) Foreign Application Priority Data
Oct. 20, 2005  (KR) .................. 10-2005-0099131

(51) Int. Cl.
A61K 31/74    (2006.01)
A61Q 19/00    (2006.01)
A61Q 19/10    (2006.01)
A61Q 5/02     (2006.01)
A61Q 19/08    (2006.01)
A61K 8/88     (2006.01)

(52) U.S. Cl.
CPC ........... *A61Q 19/08* (2013.01); *A61Q 19/00* (2013.01); *A61Q 19/10* (2013.01); *A61Q 5/02* (2013.01); *A61K 8/88* (2013.01); *A61K 2800/782* (2013.01)
USPC .................. 424/78.05; 424/78.02

(58) Field of Classification Search
None
See application file for complete search history.

(56) References Cited

U.S. PATENT DOCUMENTS
2003/0104064 A1 * 6/2003 Sung et al. ............. 424/486

FOREIGN PATENT DOCUMENTS

| EP | 0 838 160 A1 | 4/1998 |
|---|---|---|
| EP | 1563831 A1 | 8/2005 |
| JP | 05-117388 | 5/1993 |
| JP | 06-092870 | 4/1994 |
| JP | 06-256220 | 9/1994 |

(Continued)

OTHER PUBLICATIONS
Patent Abstract of Japan for publication 06-322358, pub. Nov. 22, 1994.*

(Continued)

*Primary Examiner* — Trevor Love
(74) *Attorney, Agent, or Firm* — Andrew D. Gerschutz; Tristan A. Fuierer

(57) ABSTRACT

The present invention relates to a hyaluronidase inhibitor containing poly-gamma-glutamic acid (PGA) as an active ingredient, a composition for maintaining skin elasticity and a composition for improving allergy, wherein each of the compositions contains PGA as an active ingredient. The inventive compositions containing PGA are effective in maintaining skin moisturization and skin elasticity by effectively inhibiting the activity of hyaluronidase which is an enzyme that degrades hyaluronic acid present in the skin dermis. Also, the compositions can relieve allergic symptoms by inhibiting the permeability of inflammatory cells.

3 Claims, 1 Drawing Sheet

(56) References Cited

FOREIGN PATENT DOCUMENTS

| | | |
|---|---|---|
| JP | 06-322358 | 11/1994 |
| JP | 07-138364 | 5/1995 |
| JP | 07-300522 | 11/1995 |
| JP | 10-251402 | 9/1998 |
| JP | 2000034217 A | 2/2000 |
| JP | 2003327540 | 11/2003 |
| KR | 1020020079889 A | 10/2002 |
| KR | 100475406 B1 | 2/2005 |
| KR | 100496606 B1 | 6/2005 |
| KR | 100517114 B1 | 9/2005 |

OTHER PUBLICATIONS

Hasabe et al. (JP 2002-145723) (pub. Nov. 7, 2000) (machine translation).*

Hasabe et al. (JP 2004-210699) (pub. Jul. 29, 2004) (Derwent abstract).*

Otsuka et al. (JP 2002-363279) (pub. Dec. 18, 2002) (machine translation).*

Correale et al. Atopic Dermatitis: A Review of Diagnosis and Treatment, American Family Physician, Sep. 15, 1999.*

C&EN, Shampoo, 2002, CENEAR, vol. 80, No. 15, p. 42 (pp. 1-4 attached from web publication).*

Vedan International, PGA new product, Jun. 14, 2004, Vedan International, pp. 1-2, http://www.vedaninternational.com/products/PGArelease.htm, last accessed, Aug. 17, 2012.*

Naoki Fujitani et al.; Inhibitory effects of microalgae on the activation of hyaluronidase; J. Appl. Phycol; 2001; 13:489.

Yoshihito Ito et al.; Glutamic Acid Independent Production of Poly(Y-glutamic acid) by *Bacillus subtillis* TAM-4; Bioscience, Biotechnology, and Biochemistry; 1996; 60:1239.

* cited by examiner

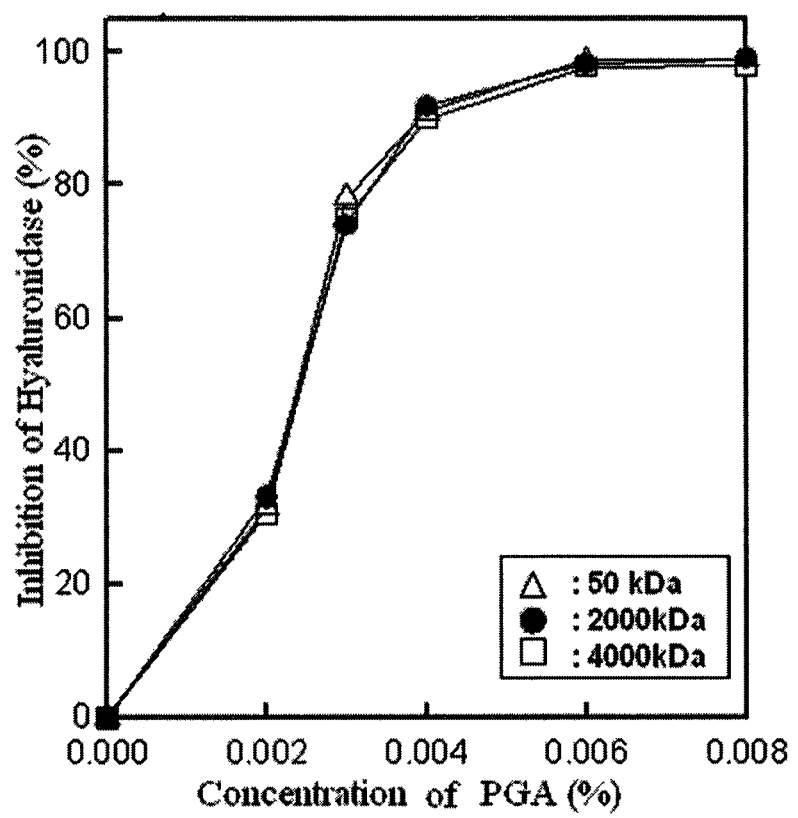

HYALURONIDASE INHIBITOR CONTAINING POLY-GAMMA-GLUTAMIC ACID AS AN EFFECTIVE COMPONENT

CROSS-REFERENCE TO RELATED APPLICATIONS

This application is filed under the provisions of 35 U.S.C. §371 and claims the priority of International Patent Application No. PCT/KR2005/003632 filed on 31 Oct. 2005 entitled "Hyaluronidase Inhibitor Containing Poly-Gamma-Glutamic Acid As An Effective Component" in the name of Sung, Moon Hee et al., which in turn claims priority of Application No. 10-2005-0099131 (KR) filed on 20 Oct. 2005, all copies of which are hereby incorporated by reference herein in their entirety.

TECHNICAL FIELD

The present invention relates to a hyaluronidase inhibitor containing poly-gamma-glutamic acid (PGA) as an active ingredient, and a cosmetic composition for maintaining skin elasticity and a composition for improving allergy, wherein each of the compositions contains PGA as an active ingredient.

BACKGROUND ART

Hyaluronidases are a family of enzymes that hydrolyze hyaluronic acid. They are carbohydrate digestive enzymes that cleave the glycoside bond of carbohydrates, and are also called "mucinases or spreading factors". The kind of hyaluronidases includes endohexosaminidase types, endoglucuronidase types, endohexosamine cleavage types and endoglucosamine cleavage types. These hyaluronidases are present in the testis or sperm of the higher animal, lysosomes of the liver, snake venom, *Klebsiella pneumoniae*, or *Streptococcus*. Meanwhile, the connective tissue of the skin comprises collagen, hyaluronic acid polysaccharide, and the like. Hyaluronidases are enzymes that degrade the hyaluronic acid, and the activation of hyaluronidases causes the hyaluronic acid of skin connective tissue to degrade, and thus, make the skin connective tissue loose to reduce skin elasticity and cause wrinkles.

In the prior art for preventing the skin connective tissue from being loose, there is a method comprising treating the skin with vitamins A, C, E, and the like to stimulate collagen synthesis and prevent oxidation. However, this method has disadvantages in that these vitamins are expensive and are easily degraded in the external environment to make their long-term storage difficult. Also, methods including applying collagen directly to the skin or orally administering collagen were suggested but have no demonstrated effects. In addition, there is a method comprising treating the skin with an extract of plants, such as *Areca catechu, Moutan cortex*, and the like, which have hyaluronidase inhibitory effects. However, this method has the disadvantage of reduced economical efficiency, because it comprises cultivating plants and extracting an active ingredient from the cultivated plants.

Meanwhile, PGA is a mucous polymer consisting of D,L-glutamic acid bound to gamma-glutamyl and is produced by microorganisms. Specifically, PGA is produced from the genus *Bacillus*. strain isolated from Chungkookjang (Korean traditional fermented soybean food prepared using rice-straw), Natto (Japanese traditional fermented soybean food), Kinema (fermented soybean food prepared in Nepal), etc. PGA produced from the genus *Bacillus* strain is an edible, water-soluble, anionic and biodegradable polymer substance, which can be used as a raw material for humectants, moisturizers and cosmetics. Recently, studies on the use of PGA to develop materials substituting for non-degradable polymers and heat-resistant plastics by esterification and produce water-soluble fibers and membranes have been performed in developed countries.

In addition, studies reported on PGA include the effect of manganese ions on the production of PGA, the use of PGA as water-soluble polymer by ultrasonic degradation, and the development of low-water-soluble plastics by the synthesis of ester derivatives (*Biosci. Biotechnol. Biochem.*, 60:1239, 1996).

In prior patents relating to the use of PGA, Japanese Patent Laid-Open Publication No. Hei 6-32742 discloses the production of PGA by *Bacillus subtillis*, and its use in health food having the effect of treating osteoporosis, such as a calcium-dissolving agent. European Patent No. 838160 discloses that PGA has the effect of reducing water contamination by reducing the content of phosphorus in water. Also, Japanese Patent Laid-Open Publication Nos. Hei 10-251402, 7-300522 and 6-322358 disclose the applications in hygienic products (e.g., diapers), food products and horticulture by preparing an absorptive and biodegradable resin with high gelatination rate and water absorption using PGA by irradiation of radiation. Also, it is known to use PGA as solidified biodegradable fibers, films or film moldings by the dissolution, precipitation and drying of PGA (Japanese Patent Laid-Open Publication Nos. Hei 7-138364 and 5-117388). In addition, the use of PGA as a polymer for drug carriers is known (Japanese Patent Laid-Open Publication Nos. Hei 6-92870 and 6-256220).

Meanwhile, the present inventors obtained a patent relating to a method for producing PGA using a halophilic *Bacillus subtilis* var. *chungkookjang* that produces PGA with high molecular weight (Korean Patent Registration No. 500,796). Also, we obtained patents relating to an anticancer composition, an immune adjuvant and an immune enhancing agent, which contain PGA (Korean Patent Registration Nos. 496, 606; 517,114; and 475,406). In addition, we have been conducting studies on another use of PGA.

Thus, the present inventors have made extensive efforts to find other functions of PGA having the above-described various effects, as a result, found that PGA inhibits hyaluronidase that degrades hyaluronic acid, which is a component of skin connective tissue, and thus it can help to maintain the elasticity of the skin, and also it has good humectant and moisturizing properties and excellent skin compatibility, thereby completing the present invention.

SUMMARY OF THE INVENTION

Accordingly, it is a main object of the present invention to provide a hyaluronidase inhibitor containing PGA as an active ingredient.

Another object of the present invention is to provide a cosmetic composition for maintaining skin elasticity, which contains PGA as an active ingredient.

Still another object of the present invention is to provide a composition for improving allergy, which contains PGA as an active ingredient.

Other features and embodiments of the present invention will be more clearly understood from the following detailed description and accompanying claims.

BRIEF DESCRIPTION OF DRAWINGS

FIG. 1 is a graphic diagram showing the hyaluronidase inhibitory activity of PGA.

DETAILED DESCRIPTION OF THE INVENTION, AND PREFERRED EMBODIMENTS THEREOF

In one aspect, the present invention provides a hyaluronidase inhibitor containing PGA as an active ingredient.

PGA according to the present invention can inhibit a hyaluronidase enzyme to prevent skin connective tissue from being loose and it has excellent skin compatibility, moisturizing and humectant properties.

In another aspect, the present invention provides a functional cosmetic composition for maintaining skin elasticity, which contains PGA as an active ingredient.

The cosmetic composition according to the present invention may be any one selected from the group consisting of moisturizer, emulsion, essence and facial cleanser.

PGA according to the present invention can relieve allergic symptoms by inhibiting the activity of a hyaluronidase enzyme, which is activated upon the development of skin inflammation to break down the structure of skin tissue and increase the permeability of inflammatory cells.

In still another aspect, the present invention provides a composition for improving allergy, which contains PGA as an active ingredient.

The composition for improving allergy according to the present invention may be any one selected from the group consisting of moisturizer, emulsion, essence, facial cleanser, hair shampoo, body shampoo, and bath treatment.

In the present invention, it was found that PGA having molecular weights of 50 kDa, 2000 kDa and 4000 kDa all had high hyaluronidase inhibitory activities, and showed similar hyaluronidase inhibitory patterns at various concentrations. This indicates that PGAs have high hyaluronidase inhibitory activities in molecular weights ranging between 50 kDa and 4,000 kDa, independent of molecular weight. Thus, the molecular weight of PGA used in the present invention is preferably in a range between 1 kDa and 10,000 kDa.

PGA used in the present invention can be produced by chemical synthesis or microbial fermentation, preferably by microbial fermentation, and more preferably by the fermentation of *Bacillus subtilis* var. *chungkookjang*.

EXAMPLES

The present invention will hereinafter be described in more detail by examples. It will however be obvious to a person skilled in the art that theses examples are for illustrative purpose only and are not construed to limit the scope of the present invention.

Example 1

Production of PGA

1% culture broth of *Bacillus subtilis* var *chungkookjang* (KCTC 0697BP) was inoculated into 3 liters of a basal medium (GS medium containing 5% L-glutamic acid: 5% glucose, 1% $(NH_4)_2SO_4$, 0.27% $KH_2PO_4$, 0.42% $Na_2HPO_4.12H_2O$, 0.05% NaCl, 0.3% $MgSO_4.7H_2O$, 1 ml/l vitamin solution, pH 6.8) for PGA production, and then cultured at a stirring speed of 150 rpm, an air injection rate of 1 vvm and a temperature of 37° C. for 72 hours. Then, the culture medium was adjusted to pH 3.0 by addition of 2N sulfuric acid solution, thus obtaining a PGA-containing sample solution.

The PGA-containing sample solution was left to stand at 4° C. for 10 hours to remove polysaccharides from the fermented solution, to which ethanol with 2 times the volume of the fermented solution was added and sufficiently mixed. The mixture solution was left to stand at 4° C. for 10 hours and then centrifuged to collect a PGA precipitate. The collected precipitate was dissolved in distilled water, and 100 μg/ml of protease was added thereto. The resulting PGA sample was left to stand in an incubator at 37° C. for 6 hours to degrade an extracellular protein present in the PGA sample. The resulting sample was dialyzed against a sufficient amount of distilled water to remove free glutamic acid and then concentrated to obtain pure PGA. The obtained PGA was measured for molecular weight using GPC (gel permeation column) and separated according to molecular weight to collect PGAs having molecular weights of 50 kDa, 2000 kDa and 4000 kDa, respectively. The collected PGAs were analyzed for hyaluronidase inhibitory effects.

Example 2

Hyaluronidase Inhibitory Activities of PGAs

Each of PGAs having 50 kDa, 2000 kDa and 4000 kDa, obtained in Example 1, was dissolved at a concentration of 1%. To 400 unit/ml of hyaluronidase, each of the PGA solutions was added to a PGA concentration of 0.002%, 0.003%, 0.004%, 0.006% and 0.008% and then allowed to react with the hyaluronidase at 37° C. for 20 minutes. Then, 0.1 mg/ml of Compound 48/80 as an activating agent, 2.5 mM of $CaCl_2$ and 0.15 M of NaCl were added to the hyaluronidase solution which have been reacted with PGA, and the mixture was allowed to react at 37° C. for 20 minutes. To the reaction solution, 0.4 mg/ml of hyalronic acid was added and reacted at 37° C. for 20 minutes. Then, the reaction was stopped by the addition of 0.4N NaOH. To the reaction solution, 3 ml of 1% p-DABA (p-dimethylaminobenzaldehyde) was added and reacted at 37° C. for 20 minutes. Then, the reaction solution was measured for enzymatic activity using the Morgan-Elson method which measures the absorbance at 585 nm. The percent inhibition of hyaluronidase activity by PGA was determined by calculating the ratio of the enzymatic activity of a hyaluronidase solution reacted with PGA to the enzymatic activity of a hyaluronidase solution unreacted with PGA (Naoki Fujitani, *J. Appl. Phycol.*, 13:489, 2001).

Inhibition (%)={1−(absorbance of hyaluronidase solution reacted with PGA-blank absorbance of hyaluronidase solution reacted with PGA)/(absorbance of hyaluronidase solution unreacted with PGA-blank absorbance of hyaluronidase solution unreacted with PGA)}×100

As a result, as shown in FIG. 1, PGAs having molecular weights of 50~4000 kDa have similar hyaluronidase inhibition activity, independent of molecular weight. In addition, they were shown to have an $IC_{50}$ value of about 0.0025% and showed an inhibitory activity of about 100% in the solution having a PGA concentration of 0.008%.

Formulations

Hereinafter, formulations of the present invention will be described with respect to moisturizer (skin), lotion (emulsion) and hair shampoo, but formulations comprising the inventive cosmetic composition will not be limited thereto.

Formulation 1: Preparation of Moisturizer Containing PGA 0.05 g of polypyrrolidone, 0.1 g of oleyl alcohol, 0.2 g of polyoxyethylene monooleate, 0.2 g of perfume, 0.1 g of methyl parahydroxybenzoate and a small amount of an antioxidant were mixed and dissolved in 8 g of 95% ethanol. The solution was mixed and stirred with a solution of 0.4 g of a 50 kDa PGA and 5 g of glycerin dissolved in 85.33 g of purified water, thus preparing moisturizer having the effect of improving skin elasticity.

Formulation 2: Preparation of Lotion (Emulsion) Containing PGA 1.2 g of ethyl alcohol, 10 g of squalan, 2 g of Vaseline, 0.2 g of ethyl parahydroxybenzoate, 1 g of glycerin monostearate, 1 g of polyoxyethylene (20M) monooleate and 0.1 g of perfume were mixed and dissolved by heating at 70° C. 0.4 g of a 2000 kDa PGA, 5 g of dipropylene glycol, 2 g of polyethylene glycol 1500, 0.2 g of triethanolamine and 76.2 g of purified water were dissolved by heating at 75° C. The two solutions were mixed with each other, and the resulting emulsion was cooled, thus preparing an oil-in-water lotion having the effect of improving skin elasticity.

Formulation 3: Preparation of Shampoo Containing PGA 15 g of sodium lauryl sulfate, 10 g of sodium laureth sulfate, 5 g of cocamidopropylene betaine, 0.1 g of disodium ethylenediaminetetraacetate and 3 g of betaine were mixed with each other. To the mixture, a solution of 0.4 g of a 4000 kDa PGA dissolved in 66.5 g of purified water was added, thus preparing shampoo having the effect of improving allergy.

Example 3

Sensory Tests of PGA-Containing Cosmetic and Compositions for Improving Allergy (1) Increase of Skin Elasticity
1. Test method
    (i) Test subjects: Fifty 30-50-year-old women (control group: 25 persons; and test group for Formulations 1 and 2: 25 persons).
    (ii) Compositions tested: The moisturizer and lotion of Formulations 1 and 2 were used in the test group, and moisturizer and lotion, which have the same compositions as in Formulations 1 and 2 but contain no PGA, were used in the control group.
    (iii) Test period: 2 months (May 2005 through June 2005)
2. Results: 22 of 25 people in the test group for the PGA-containing compositions answered that the skin conditions were improved.

TABLE 1

Measurement results for functionalities of PGA-containing compositions

|  | Control group | Formulations 1 and 2 |
|---|---|---|
| Increases of skin elasticity and moisturizing effect | 4 | 22 |
| No change | 21 | 3 |

(2) Improvement of Allergy
1. Test method
    (i) Test subjects: thirty children (younger than 13 years old) suffering from atopic skin disease. Control group: 15 persons; and test group for Formulation 3: 15 persons.
    (ii) Composition tested: the shampoo of Formulation 3 was used in the test group, and shampoo, which has the same composition as in Formulation 3 but contains no PGA, was used in the control group.
    (iii) Test period: two months (May 2005 through June 2005)
2. Results: 8 of 15 persons in the test group for the PGA-containing shampoo answered that symptoms, such as itching, were relieved.

TABLE 2

Measurement results for functionality of PGA-containing shampoo

|  | Control group | Formulation 3 |
|---|---|---|
| Relief of atopic symptoms | 0 | 8 |
| No change | 15 | 7 |

Although specific embodiments of the present invention have been described in detail above, those skilled in the art will appreciate that these descriptions are only intended to give preferred embodiments and are not construed to limit the scope of the present invention. Accordingly, the substantial scope of the present invention will be defined by the appended claims and equivalents thereof.

INDUSTRIAL APPLICABILITY

As described above, the present invention provides the hyaluronidase inhibitor containing PGA as an active ingredient, and the composition for maintaining skin elasticity and the composition for improving allergy, wherein each of the compositions contains PGA as an active ingredient. The inventive compositions containing PGA are effective in maintaining skin moisturization and skin elasticity by effectively inhibiting the activity of hyaluronidase which is an enzyme that degrades hyaluronic acid present in the skin dermis. Also, the compositions can relieve allergic symptoms by inhibiting the permeability of inflammatory cells.

What is claimed is:

1. A method of inhibiting hyaluronidase activity using a composition comprising poly-gamma-glutamic acid (PGA) as an active ingredient, wherein the molecular weight of the PGA is 4,000 kDa to 10,000 kDa, wherein the composition further comprises one or more of the compounds selected from the group consisting of petroleum jelly, ethyl parahydroxybenzoate, glycerin monostearate, polyoxyethylene monooleate, sodium lauryl sulfate, sodium laureth sulfate, and disodium ethylenediaminetetraacetate, and wherein the PGA is produced from *Bacillus subtilis* var *chungkookjang*, the method comprising administering the composition to a subject in need of inhibition of hyaluronidase activity.

2. The method according to claim 1, wherein the composition is any one selected from the group consisting of moisturizer, emulsion, essence, facial cleanser, hair shampoo, body shampoo, and bath treatment.

3. The method of claim 2, wherein said composition is an emulsion comprising one or more of the compounds selected from the group consisting of petroleum jelly, ethyl parahydroxybenzoate, glycerin monostearate, and polyoxyethylene monooleate.

* * * * *